United States Patent

Blyakhman

[11] Patent Number: 5,191,088
[45] Date of Patent: Mar. 2, 1993

[54] AROMATIC MONOANHYDRIDE-ESTERS

[75] Inventor: Yefim Blyakhman, Bronx, N.Y.

[73] Assignee: Ciba-Geigy Corporation, Ardsley, N.Y.

[21] Appl. No.: 791,863

[22] Filed: Nov. 13, 1991

Related U.S. Application Data

[63] Continuation-in-part of Ser. No. 667,728, Mar. 11, 1991, abandoned.

[51] Int. Cl.$^5$ .......................................... C07D 405/12
[52] U.S. Cl. ...,.................................................. 548/435
[58] Field of Search ......................................... 548/435

[56] References Cited

U.S. PATENT DOCUMENTS

| | | | |
|---|---|---|---|
| 4,079,041 | 3/1978 | Baumann et al. | 548/525 |
| 4,132,716 | 1/1979 | Kvita et al. | 548/435 |
| 4,233,220 | 11/1980 | Kvita et al. | 548/435 |
| 4,604,437 | 8/1986 | Renner | 526/262 |
| 4,742,166 | 5/1988 | Renner | 548/435 |
| 5,071,941 | 12/1991 | Lubowitz et al. | 548/435 |
| 5,082,905 | 1/1992 | Lubowitz et al. | 548/435 |
| 5,087,701 | 2/1992 | Lubowitz et al. | 548/435 |

FOREIGN PATENT DOCUMENTS

| | | |
|---|---|---|
| 152372 | 8/1985 | European Pat. Off. |
| 166693 | 1/1986 | European Pat. Off. |
| 0277476 | 8/1988 | European Pat. Off. |
| 0289798 | 11/1988 | European Pat. Off. |
| 0323540 | 7/1989 | European Pat. Off. |
| 0355435 | 2/1990 | |

OTHER PUBLICATIONS

Derwent Abst. 85-204936/34.
Derwent Abst. 86-008853/02.

Primary Examiner—Mary C. Lee
Assistant Examiner—Mary Susan H. Gabilen
Attorney, Agent, or Firm—JoAnn Villamizar

[57] ABSTRACT

Aromatic monoanhydride-esters of the formula (I)

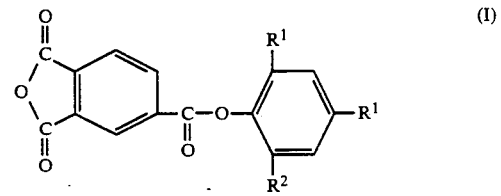

wherein $R^1$ is

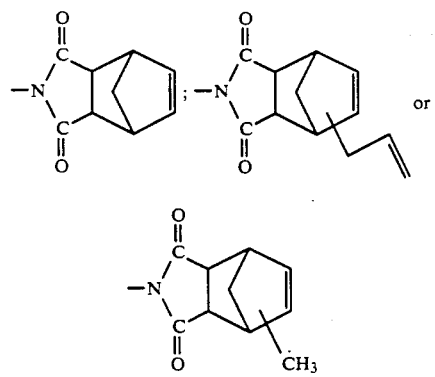

and $R^2$ is hydrogen, $C_1$–$C_4$alkyl or —$OCH_3$ are useful as endcapping agents for the synthesis of multifunctional high temperature resins such as polyimides, polyimide-esters, polyimide-ethers and polyimide-amides.

2 Claims, No Drawings

AROMATIC MONOANHYDRIDE-ESTERS

BACKGROUND OF THE INVENTION

This application is a continuation-in-part of parent application Ser. No. 07/667,728 filed Mar. 11, 1991, now abandoned.

Addition type thermoset polyimide, polyimide-amide, polyimide-ester resins are finding use as matrix resins for advanced composites, adhesives, coating and other applications. These resins generally contain two reactive end groups per molecule such as acetylene, norbonene and maleimide. In order to increase the glass transition temperature and improve thermal performance of cured resin, it is desirable to increase functionality of the resins.

One approach is the use of encapping agents having two unsaturated groups in the molecule as taught in U.S. Pat. No. 4,233,220 wherein bis-maleimidophthalic anhydride of the formula

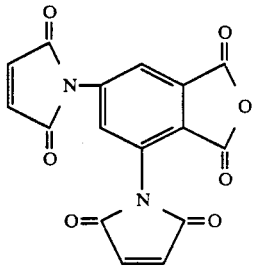

is disclosed. This compound could be used for the synthesis of tetrafunctional polyimides with bismaleimido phenyl end groups but the synthesis of the monomer is a complex multistep process resulting in a low yield of the product (<20%). Additionally, attachment of anhydride and both maleimido groups to the same nucleus creates steric hindrance and reduces reactivity of the end groups in the curing process.

Accordingly, it is an object of the present invention to provide new multifunctional monomers which can be used for the synthesis of reactive polyimides, polyimide-esters, polyimide-ethers and the like having increased functionality and, thus, improved glass transition temperature.

Various other objects and advantages of this invention will become apparent from the following description thereof.

SUMMARY OF THE INVENTION

The present invention relates to aromatic mono-anhydride-esters having two unsaturated reactive groups in a molecule for use as endcapping agents in the synthesis of multifunctional high temperature resins.

DETAILED DESCRIPTION OF THE INVENTION

The present invention relates to aromatic monoanhydride-esters of the formula I

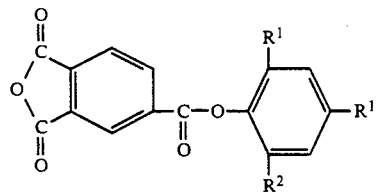

wherein $R^1$ is

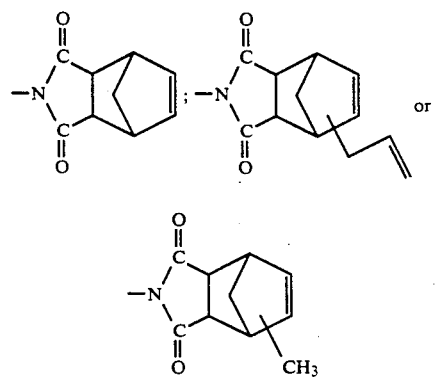

and $R^2$ is hydrogen, $C_1$-$C_4$ alkyl or $-OCH_3$; preferably $R^2$ is hydrogen.

The monoanhydride-esters of the present invention can be prepared by reaction of trimellitic anhydride chloride with phenols having two unsaturated groups as exemplified in the reaction scheme below:

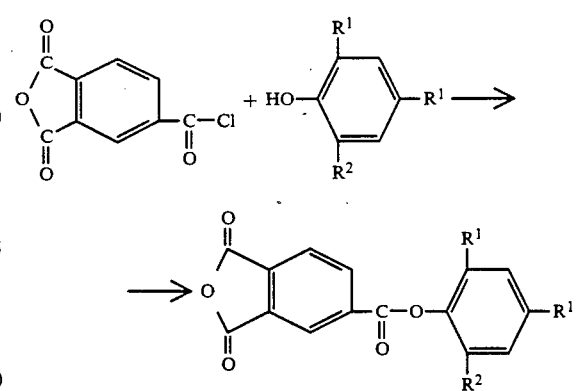

Phenols having two unsaturated imido (nadic, methyl nadic, allylnadic) groups in a molecule may be obtained by reaction of diaminophenol with corresponding anhydride.

Reaction between trimellitic anhydride chloride and the phenols may be carried out in anhydrous solvents, such as ether, tetrahydrofuran, acetone, methylethyl ketone, benzene, toluene, ethylene dichloride etc., in the presence of tertiary amines such as pyridine, triethylamine, etc. Preferably, the tertiary amine is added to a solution of trimellitic anhydride chloride and a phenol cooled to 0°–5° C. and subsequent stirring of the reaction mixture at 15°–75° C. for 0.5–6 hrs. The obtained anhydride-ester may be separated by precipitation in a solvent in which tertiary amines' salts are soluble, e.g., methanol, ethanol, 2-propanol.

The multifunctional high temperature resins contain, per molecule, on average 2–3 aromatic monoanhydride-ester groups of the formula I set forth hereinabove.

The polymers according to the present invention can be manufactured according to methods of synthesis which are known for the manufacture of macromolecules which have pendant side groups. In principle, the polyimides, polyimide-esters, polyimide-ethers, polyimide-amides and routes disclosed in U.S. Pat. No. 4,079,041, which is hereby incorporated by reference, can be used.

EXAMPLES

The following examples serve to give specific illustration of the practice of this invention, but they are not intended in any way to limit the scope of this invention.

EXAMPLE 1

Synthesis of 2,4-dinadicimidophenol 315.2 g (1.6 mol) of 2,4-diaminophenol dihydrochloride are dissolved in 2 lt of DMAc and neutralized by 268.8 g (3.2 mol) of $NaHCO_3$ at 60° C. under $N_2$. After that the mixture is cooled to room temperature and 525.2 g (3.2 mol) of 5-norbornene-2,3-dicarboxylic (nadic) anhydride and 400 ml of toluene are added. The reaction mixture is refluxed with a Dean-Stark trap to remove water. Then toluene is distilled off, the reaction mixture is filtered, and the filtrate precipitated in water at 1:5 ratio. The precipitate is washed with 3 times and dried in a vacuum-oven at 90° C. 2,4-dinadicimido phenol has a melting point of 263°–265° C., its IR and NMR spectra are consistent with proposed structure and its purity is 95% by HPLC.

EXAMPLE 2

Synthesis of Monoanhydride-ester of the Following Structure

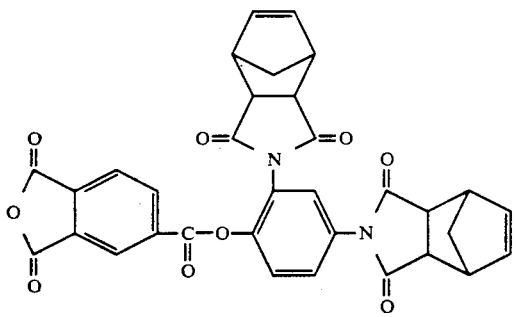

To a solution of 105.3 g (0.5 mol) of trimellitic anhydride chloride and 208.4 g (0.5 mol) of 2,4-dinadicimido phenol in 2 lt of dry acetone cooled to 0° C. 43.5 g (0.55 mol) of pyridine are added dropwise (30 min). After that the reaction mixture is stirred 2 hrs. at 20° C. and 1 hr. at 50°–55° C. The mixture is cooled to 15° C. and filtered. The filtrate is mixed with 4 lt of anhydrous isopropanol in a blender and formed precipitate is washed with ether and dried in a vacuum over at 80° C. Yield is 280 g (95%). Obtained product-a white powder-has a melting point of 276°–277° C. Its IR and NMR spectra are consistent with proposed structure. N-phenyl imide of the anhydride is obtained by reaction of 1 mole of the anhydride with 1 mole of aniline. Structure of the derivative is confirmed by IR and NMR spectra.

EXAMPLE 3

Synthesis of polyimide-ester

Monomers used:

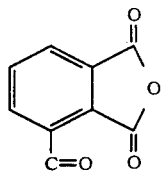

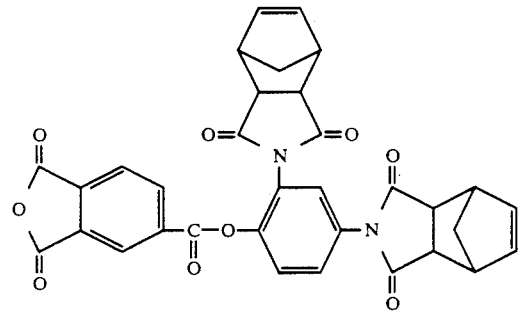

Trisanhydride (I)

Monoanhydride-ester having two nadic imido groups (II)

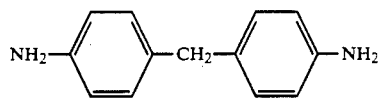

Methylenedianiline (III)

A solution of 59.5 g (0.3 mol) of methylenedianaline (III) in 1200 ml of N,N-dimethylacetamide is cooled to 0° C. and 64.8 g (0.1 mol) of the trisanhydride I is added over 1.5 hrs. in 10 g portions under $N_2$ with vigorous stirring while the temperature is maintained below 0° C. 177.8 g (0.3 mol) of the monoanhydride II is then added and the reaction mixture stirred overnight at room temperature. To the resulting solution, 500 ml of toluene is added and the mixture refluxed with a Dean-Stark trap for 3 hrs. Then, the toluene is distilled off and the solution heated at 163°–165° for 5 hrs. After cooling, the solution is precipitated in 5 lt of methanol and the obtained yellow powder is dried in a vacuum-oven. The yield of the polyimide-ester is 178 g. The polymer exhibits a $T_g$ of 223° C. (determined by DSC) and an intrinsic viscosity of 0.08 dl/g (NMP, 25° C.). The polyimide-ester undergoes polymerization upon heating to 300° C.

EXAMPLE 4

Synthesis of 2,4-di(methylnadicimido)phenol 197.1 g (1 mole) of 2,4-diaminophenol dihydrochloride is dissolved in 2 liters of DMAc and neutralized with 168 g (2 moles) of $NaHCO_3$ at 60° C. under $N_2$. The mixture is then cooled to room temperature and 356.4 g (2 moles) of methyl-5-norbornene-2,3-dicarboxylic anhydride and 300 ml of toluene are added. The reaction mixture is refluxed with a Dean-Stark trap to remove water. After that toluene is distilled off, the reaction mixture is filtered and the filtrate precipitated in water at a 1:7 ratio. The precipitate is washed 5 times with water and dried in a vacuum-oven at 80° C. The yield is 404.8 g (91%) and the structure of the obtained 2,4-di(methylnadicimido)phenol is confirmed by IR and NMR and its purity is 93% by HPLC.

EXAMPLE 5

Synthesis of Monoanhydride-ester of the Following Structure

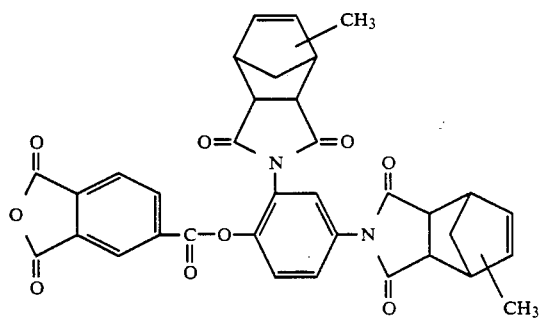

To a solution of 210.6 g (1 mol) of trimellitic anhydride chloride and 444.8 g (1 mol) of 2,4-di(methylnadicimido)phenol in 3.5 liters of dry acetone cooled to 0°, 111.3 g (1.1 mol) of triethylamine are added dropwise (1 hr). After that the reaction mixture is stirred 2.5 hrs at room temperature and 1 hr at 50°-55° C. The mixture is cooled to 10° C. and filtered. The filtrate is mixed with 6 lites of anhydrous isopropanol and the precipitate formed is washed with ether and dried in a vacuum-oven at 60° C. The yield is 569.4 g (92%). The IR and NMR spectra of the obtained product are consistent with the proposed structure. N-phenylimide of the monoanhydride-ester is synthesized by reaction of 1 mole of the anhydride with 1 mole of aniline. The structure of the derivative is confirmed by IR and NMR.

What is claimed is:

1. An aromatic monoanhydride-ester of the formula I

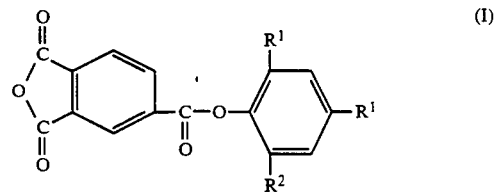

wherein $R^1$ is

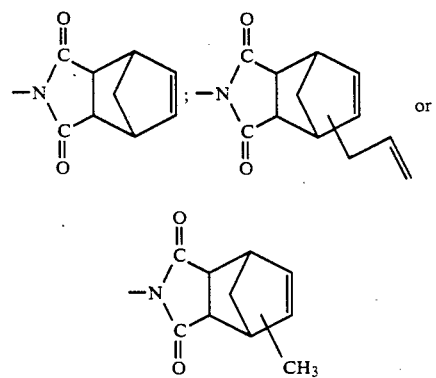

and $R^2$ is hydrogen, $C_1$-$C_4$alkyl or $-OCH_3$.

2. An aromatic monoanhydride-ester according to claim 1 wherein $R^2$ is hydrogen.

* * * * *